United States Patent [19]

Koll

[11] Patent Number: 5,031,635
[45] Date of Patent: Jul. 16, 1991

[54] PLASTIC MOLDED BIOLOGICAL SAMPLE COLLECTION SWAB

[75] Inventor: Laurel A. Koll, Ruleville, Miss.

[73] Assignee: Accu-Med Corporation, Ruleville, Miss.

[21] Appl. No.: 574,517

[22] Filed: Aug. 27, 1990

Related U.S. Application Data

[63] Continuation of Ser. No. 425,447, Oct. 23, 1989, abandoned, which is a continuation of Ser. No. 8,320, Jan. 29, 1987, abandoned, which is a continuation-in-part of Ser. No. 677,732, Oct. 3, 1984, Pat. No. 4,653,510, which is a continuation-in-part of Ser. No. 353,220, Mar. 19, 1982, Pat. No. 4,485,824.

[51] Int. Cl.$^5$ ............................................. A61B 10/00
[52] U.S. Cl. ..................................... 128/756; 128/759
[58] Field of Search ............... 128/758, 755, 756, 759, 128/757; 604/1, 221, 222; 435/295, 296

[56] References Cited

U.S. PATENT DOCUMENTS

| | | | |
|---|---|---|---|
| 2,591,927 | 4/1952 | Gladstone | 128/759 |
| 3,179,108 | 4/1965 | Block et al. | 604/1 |
| 3,618,609 | 11/1971 | Glick | 604/1 |
| 3,640,268 | 2/1972 | Davis | 128/759 |
| 3,818,911 | 6/1974 | Fournier | 604/1 |
| 3,871,375 | 3/1975 | Bennett | 604/1 |
| 3,877,464 | 4/1975 | Vermes | 128/759 |
| 4,136,680 | 1/1979 | Southworth | 128/759 |
| 4,157,709 | 6/1979 | Schuster et al. | 128/759 |
| 4,485,824 | 12/1984 | Koll | 128/756 |
| 4,653,510 | 3/1987 | Koll | 128/756 |
| 4,735,214 | 4/1988 | Berman | 128/759 |

Primary Examiner—Kyle L. Howell
Assistant Examiner—Robert L. Nasser, Jr.
Attorney, Agent, or Firm—Nixon & Vanderhye

[57] ABSTRACT

A porous molded plastic swab construction for microbiological or other use including a swab element attached to an elongated carrier member. The swab is constructed from molded porous plastic materials such as high density polyethylene, ultra-high molecular weight polyethylene, polypropylene, polyvinyledene fluoride, ethylene-vinyl acetate, styrene-acrylonitrile, polytetrafluoroethylene and silicone rubber having a pore size of from about 10 to about 2,000 microns with a density of about 35% to about 60% void volume. The swabs are designed for incorporation into specimen collection instruments, or for individual use as collectors or applicators.

26 Claims, 2 Drawing Sheets

PLASTIC MOLDED BIOLOGICAL SAMPLE COLLECTION SWAB

BACKGROUND OF THE PRESENT INVENTION

This application is a continuation of my co-pending application Ser. No. 07/425,447 filed Oct. 23, 1989 and now abandoned, which in turn is a continuation of application Ser. No. 07/008,320 filed Jan. 29, 1987 and now abandoned, which in turn is a continuation-in-part of application Ser. No. 06/677,732, filed Oct. 3, 1984, and now U.S. Pat. No. 4,653,510, which is in turn a continuation-in-part of my co-pending application Ser. No. 06/353,220, filed Mar. 1, 1982, and now U.S. Pat. No. 4,485,824. The entire disclosures of these parent applications are hereby expressly incorporated by reference.

This invention is generally directed to apparatus for collecting, depositing, transporting and/or growing protective biological specimens. It is particularly directed to a new, biologically inert swab construction which may be used with the devices disclosed in my earlier filed parent applications. It will be appreciated, however, that the swab of this invention may be used as an applicator or depositor, as well as a collector of bacteriological specimens or other materials apart from these devices, in much the same manner as conventional swabs are used.

It has been found that conventional cotton swabs and wound rayon filament swabs are not completely satisfactory as bacteria collection mechanisms. The new swab according to this continuation-in-part application is constructed from porous plastic material which can be molded to any desired shape, pore size and texture. The preferred porous plastic materials are not new per se. They have been used in industry and in medicine for various applications such as: inline filters, aeration diffuser tubes, under drain support plates, pneumatic mufflers, intake filters, marker pin nibs, biomedical and blood serum filters, catheter vents, etc. However, these materials have not heretofore been used in construction of biological swabs or applicators as disclosed further herein.

The preferred materials suitable for use in the construction of swabs according to this invention are porous plastics such as high density polyethylene, ultra-high molecular weight polyethylene, polypropylene, polyvinyledene fluoride, ethylene-vinyl acetate, styrene-acrylonitrile, polytetrafluoroethylene, silicone rubber, etc.

One of the more advantageous features of this invention is that the porous plastic materials can be molded to exacting shape and size, with very close tolerances. As a result, precision swabs may be designed that will produce exact duplication of results, and that will work reliably in precision instruments, such as the devices disclosed in my earlier filed applications. This precision characteristic is also important from an esthetic standpoint insofar as exacting size and shape assures the user of a very professional and quality product. Moreover, the wide choice of materials allows a swab design that can be tailored for virtually any intended microbiological, or other use.

Moreover, because the swabs are formed in precision molds, not only size, but also volume and density can be controlled very exactly. As a result, the new swabs absorb and release bacteria, and/or other liquids very well, and they are not toxic to the bacteria. This exactness permits use of the swabs for quantitative sampling and depositing, with extreme precision that heretofore was unobtainable with conventional swabs or applicators. In this regard, liquid seems to flow equally well both to and from the swab so that the swabs will pick up exacting amounts, or will release exacting amounts, depending or whether the swab is used as an applicator or collector. The naturally hydrophobic swabs may be used to absorb only non-aqueous products. However, the swabs may be treated so as to exhibit hydrophilic characteristics and to therefore absorb aqueous products, as well.

Another advantage of this invention is that the swabs can be attached to rods or tubes of similar material with molecular interaction by ultrasonic or other welding methods, without the use of adhesives, solvents or harmful chemicals or reagents that are potentially toxic to fragile microorganisms. In addition, fusion of the swab to the mounting rod minimizes the probability of the swab coming off inside a human or animal body cavity. Alternatively, the resiliency of the preferred materials makes possible an excellent compression fit without welding, when desired.

The unique swab construction according to this invention also allows the use of gamma irradiation or electro beam sterilization that has a degrading effect on many adhesives. Moreover, the materials mentioned above as suitable for the swab construction have physical characteristics that allow them to withstand the pressure and temperature of autoclave sterilization, which is very cost effective and widely used in the medical industry.

The plastic swab of this invention is highly absorbent and highly porous. Because of its high porosity, the swab material gently scrapes the tissue, causing microscopic particles to be picked up and gathered into the pores of the swab. This assures a much better sample for both culture and cytological use than absorbency alone.

The inertness of the preferred plastic materials is ideally suited for microbiological use, since the fragile microorganisms remain unaffected. The high temperatures required for molding the swabs produce a biologically inert swab that requires considerably much less handling to achieve the end product. Thus, the swab is sterile when made, and needs only to be assembled on an associated rod or tube by a welding procedure or a simple compression fit, which can be done with automatic assembly machinery within a controlled environment. By contrast, a common cotton or synthetic filament swab must be first extruded into filament form (in the case of the synthetic material), spun or combed into some usable configuration, and then wrapped or spun onto the rod and fixed in some manner. The fineness of the filaments and the many more steps in processing have a much greater potential for microbiological contamination. And even though these microorganisms are later killed by sterilization, their remains are present in the form of available protein. The live bacteria that are acquired in the specimen collection procedure can feed on this protein which, in many cases, is undesirable. For example, it is sometimes as many 48 hours after collection before a laboratory can culture the specimen. Many specimens are placed in transport medium for transport to the lab. Some of the most common flora may be more prolific than many of the pathogenic microorganisms. If the bacteria are placed in an environment containing protein, they may proliferate to a state different from that of the culture site. This would, of course, produce an unrealistic culture. In the case of the instruments disclosed in my earlier filed applications, the bacteria are placed into transport media without exposure to air or any bacteria other than that found in the exact culture site. Any available protein therefor would be detrimental to obtaining a true and exact sampling of the culture site.

In accordance with the present invention, it is possible to produce a collection swab that is biologically superior to existing swabs and thereby achieve a great improvement over existing conventional swab constructions. Additionally, since the swabs according to this invention are molded in one piece, it is very much less likely that any part of the swab will remain in the human or animal body cavity where the specimen was obtained. With conventional swabs made of several thousand strands, a small piece of filament is much more likely to remain in the body cavity, thereby creating the possibility of infection.

Another advantage of the swab construction in accordance with this invention is the reduction in manufacturing costs. The design disclosed herein is much more adaptable to automatic assembly in a closely controlled environment which not only reduces the possibility of contamination, but also reduces costs. Thus, it is possible to economically manufacture a swab completely without the presence of oxygen, which is necessary for the culturing of strictly obligatory anaerobes, particularly when used with the instruments disclosed in my earlier applications.

These and other objects and advantages of this invention will be better understood by reading the following detailed description of the presently preferred exemplary embodiments taken in conjunction with the accompanying drawings, of which:

Figure 4:
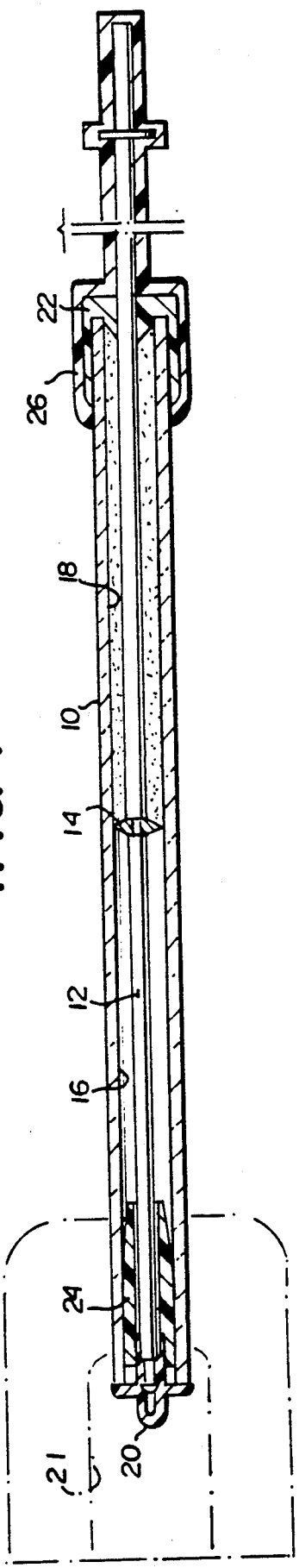
Figure 5:
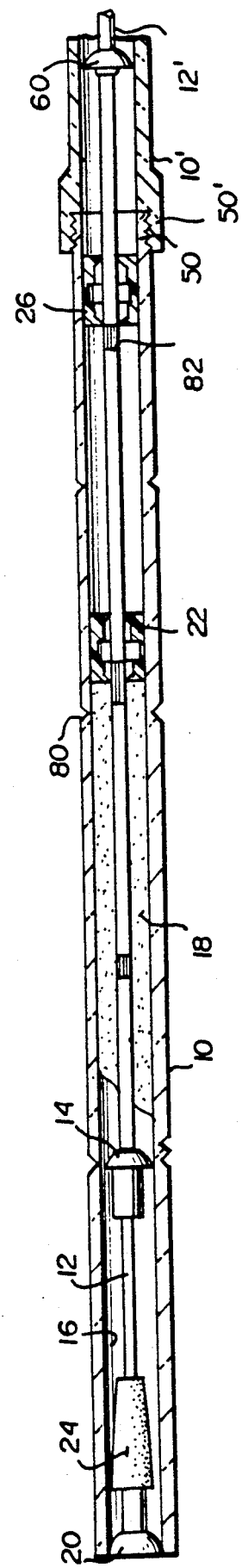

FIG. 4 is a partial cross-sectional view of the earlier preferred exemplary embodiment of a collection instrument as disclosed in my above referenced U.S. Pat. No. 4,485,824, and which includes a swab element in accordance with an exemplary embodiment of this invention;

FIG. 5 is a partial cross-sectional view of the preferred exemplary embodiment of a collector instrument disclosed in the above-referenced most recently filed application, and which includes a swab element in accordance with an exemplary embodiment of this invention.

Figure 1:
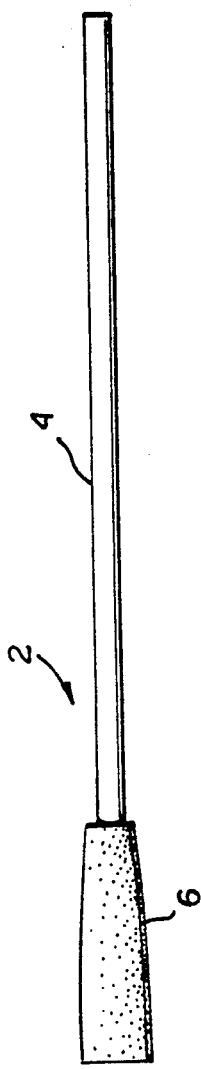
FIG. 1 is side view of a swab according to an exemplary embodiment of the invention.

Referring now to FIG. 1, there is shown a biologically inert swab 2 which includes an elongated rod or tube 4 having a swab element 6 mounted on one end thereof. The swab element 6 is constructed of porous plastic material, and preferably a polymer such as high density polyethylene, ultra-high molecular weight polyethylene, polypropylene, polyvinyledene fluoride, ethylene-vinyl acetate, styrene-acrylonitrile polytetrafluoroethylene, or silicone rubber, etc. Pore sizes may range from about 10 to about 2,000 microns with a density of 35% to 60% void volume. The hardness of the chosen materials may range from soft through resilient to rigid, and the materials are chemically inert to most chemicals and solvents. Temperature resistance ranges from −100° to 350° F. Hydrophylic treatment may be utilized in the manufacture of the swabs to enhance the acceptance of aqueous products. Conversely, hydrophobic swabs may be used to absorb only non-aqueous products, a feature that was heretofore unobtainable with conventional swabs or applicators. The materials are naturally white in color but can easily be colored or shaded to exact specifications.

The swab is molded in precision molds to exacting shape and size with very close tolerances. The swab element 6 may be solid, or provided with an internal bore, and may be attached to the rod or tube 4 preferably by ultrasonic welding or other suitable welding methods, or merely by compression fit. Alternatively, the swab element and elongated rod or stem may be molded as a single, solid unit. If desired, a stiffening element may be molded into the elongated tube or rod portion 4. It is important to note that the use of adhesives, solvents, or other means which could otherwise be toxic to fragile microorganisms is not required. Ultrasonic welding is particularly desirable where the tube or rod is of the same or similar material as the swab element. It will be appreciated, of course, that the tube or rod need not be of the same material as the swab element.

The swab illustrated in FIG. 1 may be utilized as a collector or as a depositor. In the collector mode, the swab may be used to obtain and transport and/or recover microorganisms, bacterial specimens, and any or all other pathogenic organisms for identification and sensitivity studies, as well as for clinical diagnoses of, for example, carcinogenic agents and the like. In short, the swab of this invention has applicability for all uses generally associated with conventional swabs.

Figure 2:
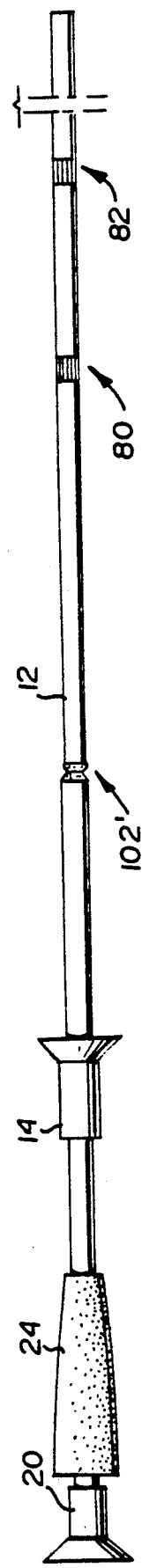
FIG. 2 is a side view of a rod subassembly for use in a preferred embodiment of a collector instrument disclosed in the above referenced most recently filed application, and as illustrated in FIG. 5 herein, and which includes a swab in accordance with an exemplary embodiment of this invention.

Turning now to FIG. 2, there is illustrated a rod subassembly for use with the preferred exemplary instrument disclosed in my earlier filed application Ser. No. 677,732 and as illustrated in FIG. 5 herein. In this preferred embodiment, the rod subassembly includes a rod or hollow tube 12, a middle seal 14, a front seal 20 and a swab element 24. Other details with respect to the rod assembly and the seal construction may be found in the disclosure of the above-referenced earlier filed application, as well as in the detailed description of FIG. 5 which appears below.

Figure 3:
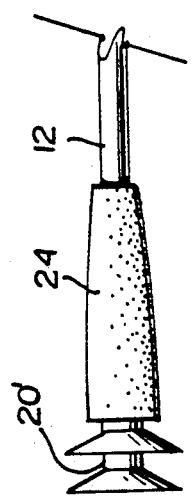
FIG. 3 is a partial side view of the rod as illustrated in FIG. 2 but wherein a double front seal arrangement is used.

In FIG. 3, there is illustrated a partial side view of rod subassembly of the type disclosed in FIG. 2 but wherein a double seal 20' is utilized in front of the swab element 24. This double seal arrangement provides greater sealing capacity between the collection zone 16 and the exterior of the instrument, and thus provides an extra measure of contamination prevention.

FIG. 4 illustrates a device in accordance with a preferred exemplary embodiment as disclosed in my above referenced U.S. Pat. No. 4,485,824. Reference is made to that patent for a more complete and detailed description of the structure and operation of the device. Generally, it includes an elongated outer protective hollow tube or cylinder 10 and an inner rod 12 having a greater length than the cylinder. Typically the rod and cylinder are made of transparent glass or plastic or the like. For purposes of illustration, the rightmost ends of the cylinder and rod assembly (which assembly might also be thought of as a piston 12 and a cylinder 10 assembly or simply as a coaxial means) will be referred to as the "rear" ends while the leftmost ends as shown in FIG. 4 will be referred to as the "forward" ends. The same relative orientation will be used throughout this application for describing relative locations along the rod and/or cylinder structures.

As may be observed in FIG. 4, the outside diameter of rod 12 is materially less than the inside diameter of the cylinder 10. There is, therefore, a coaxial space created between the rod and cylinder in which various materials may be contained. This coaxial space is subdivided by various seals into a series of chambers. For example, a specimen capturing zone or chamber 16 is defined between a flexible front seal 20 affixed to the front end of rod 12 and a flexible middle seal 14 also affixed to rod 12 at a position spaced rearwardly of the front seal 20. This specimen collection zone 16 includes an absorbent specimen collection swab 24 constructed in accordance with this invention and attached to or integrally formed with the rod 12. Before use, chamber 16 is sealed from outside contaminants by the front seal 20.

A second chamber 18 is also defined between the middle seal 14 and a rear seal 22 which is fixedly attached to cylinder 10 rearwardly of the middle seal 14. Chamber 18 typically contains a culture growth medium, a culture transport medium, a biological release agent or the like. As further shown in FIG. 4 by stippling, said medium may, for example, fill substantially all of chamber 18. The remainder of chamber 18 and of chamber 16 may be filled with a non-contaminated, non-reactive gas or liquid.

After the distal end of the entire structure is inserted to a desired site of a biological specimen (for example, deep within an internal organ 21 of a human or animal), the rod 12 is moved forwardly so as to expose the collection zone 16 and the swab 24 to the desired biological specimen. It should be observed by moving rod 12 forwardly, the volume of cavity 18 has been increased while 16 has been unsealed so as to permit capture of the desired biological specimen. The disk-like middle seal 14 has a flexible periphery that may be chosen to have a desired degree of stiffness by choosing its thickness, material, etc. as will be appreciated. In some embodiments, it may be desirable to make the periphery of disk-like middle seal 14 quite flexible such that part of the inert filling from chamber 16 will actually flex the periphery of the middle seal 14 and pass into chamber 18 when the rod is moved forwardly thus relieving a relatively lower pressure chamber 18 caused by forward movement of rod 12. On the other hand, in other embodiments it may be desired to make the disk-like seal somewhat stiffer in its periphery so as to leave a relatively lower pressure in chamber 18 as the rod 12 is moved forwardly. In this latter instance, when the rod 12 is again moved rearwardly so as to compress the contents of chamber 18, a relatively lower pressure area may be created to chamber 16 so as to draw additional volumes of biological specimen into that chamber.

Typically, when the instrument has rod 12 moved forwardly so as to capture a biological specimen, the operator will be holding the rear end of the assembly and thereby be able to move the distal end of the extended and opened assembly within the internal organ so as to insure absorption of the desired biological specimen within the swab construction 24. Thereafter, rod 12 is moved rearwardly and the front seal 20 inverts so as to provide sliding and sealing contact to the inside walls of the cylinder 10.

The volume of chamber 18 is necessarily reduced by continued rearward movement of rod 12 (for example, after removal from the body organ). This produces a pressure build up of the desired biological medium in chamber 18 until the periphery of the disk-like middle seal is flexed to permit the prefilled material in chamber 18 to pass into contact with the captured biological specimen in chamber 16. As will be appreciated, any excess material in the now shrinking combined volume of chambers 18 and 16 is also permitted to pass outwardly past the inverted cap-like front seal 20.

In this manner, a desired biological specimen may be captured at its natural site and transferred to a desired medium or the like within the coaxial seal of the chambers 16 and 18.

The only conceivable source of contamination might be via the rearward normally extended surface of rod 12. If this surface should become contaminated, then it is conceivable that some contamination might pass rear seal 22 and into the biologically active chamber 18 as the rod is moved forwardly. In the embodiment of FIG. 4 such possible contamination is prevented by a thin protective outer or barrier seal 26. This thin outer seal 26 may be provided, for example, in the form of a dipped coating of a medical grade elastomer to a point past the forward end of the rear seal 22. This thin layer of elastomer or the like may be then be simply stripped from the rod by the Chevron-type rear seal as the rod is moved forwardly to the outer tubes so as to pile up against the rear seal during forward rod movement. During subsequent rearward rod movement, the thin flexible seal 26 may break or otherwise lose its sealing properties. However, such would be of no consequence since the inside pressure of the assembly is then above the ambient thus preventing inward passage of materials past the seals and the like. Furthermore, there is no further contemplated forward movement of the rod after the barrier seal 26 might be broken.

In FIG. 5 there is illustrated an improved exemplary embodiment as disclosed in my most recent filed application, Ser. No. 677,732. As in the FIG. 4 embodiment, there is an inner rod 12 slidably contained within a larger coaxial space 10. A flexible front seal 20 and middle seal 14 are fixed toward the forward end of rod 12 so as to define a specimen capturing zone or chamber 16 therebetween. An absorbent specimen collection swab element 24, of the type disclosed in this continuation-in-part application, is ultrasonically welded or compression fit about the rod 12 within the area between the front seal 20 and middle seal 14. As previously indicated, the swab element and rod 12 may be molded as a single, solid unit. Rear seal 22 has now been moved inside and forwardly of cylinder 10. However, it still defines a second medium containing chamber 18 between it and the middle seal 14. Barrier seal 26 is, in this embodiment, now constructed to be identical unto the rear seal 22 and is spaced rearwardly thereof by a distance that is at least equal to the maximum forward travel of rod 12 during the specimen capturing procedure. In this manner, a limited section of rod 12 which moves forwardly through rear seal 22 into the biologically active zone 18 is protected by a third chamber between seals 22 and 26.

Since chambers 16 and 18 can now both be disposed toward the front end of cylinder 10 in standardized positions, the biologically active portions of the device may be made in a standard size module. For some applications, this may be of a suitable size for end usage. For other applications (for example, for equine uterine culture collections), a considerably longer structure may be physically required for access to the desired biological site. If so, then a reusable (or disposable) cylinder extension 10' and/or a reusable (or disposable) rod extension 12' may be operatively attached to cylinder 10 and rod 12 respectively. For example, as depicted in FIG. 5, the rear end of cylinder 10 may include a threaded portion 50 which meets with a threaded portion 50' of a cylinder extension 10' of suitable length. Similarly, a ball and socket-type coupling 60 or the like may be utilized to connect the ends of rod 12 and the rod extension 12' is also depicted in FIG. 5. Other types of conventional mechanical couplings may also be utilized for such connections of the extension 10' and 12' as should be appreciated.

The operation of the active standard-sized module is similar to that of my earlier preferred embodiment illustrated in FIG. 4. It will be understood that additional details as to the operation of the device illustrated in FIG. 5 may be found in my application, Ser. No. 677,732.

In addition to using the swab as disclosed in this continuation-in-part application in conjunction with the collection devices disclosed in my earlier filed applications, it will be appreciated that the swab may be used for a variety of other purposes. For example, the swab disclosed herein may be used in microbiological testing which involves absorption as well as release of bacteria in a controlled and predictable manner. As earlier indicated, because the swabs constructed in accordance with this invention are molded in precision molds, their size, volume and density can be controlled very exactly. Dry weights, for example, are within 200ths of a grain. Wet weights vary within 100ths of a grain. This exactness permits the use of the swabs disclosed herein for quantitative sampling and depositing, etc. with extreme precision that heretofore was unobtainable with swabs or applicators of the conventional type. It is to be noted in this regard that the absorption and wicking action is very precise and that liquid flows equally well in both directions, i.e., both to and from the swab.

While the swab construction of this invention has been disclosed in what is presently regarded as its most exemplary embodiment, those skilled in the art will recognize that many modifications and variations may be made while still retaining many of the advantages and novel features of the invention. Accordingly, all such modifications and variations are intended to be included within the scope of the following claims.

What is claimed is:

1. A biologically inert swab for obtaining a specimen comprising:
    a) an elongated carrier member;
    b) a molded, porous plastic swab element connected to one end of said carrier member, said swab element formed with a pore size of about 10 to about 2,000 microns, and a density of about 35% to about 60% void volume, said swab element constructed of plastic material selected from the group consisting essentially of high density polyethylene, ultra-high molecular weight polyethylene, polypropylene, polyvinyledene fluoride, ethylene-vinylacetate, styrene-acrylonitrile, polytetrafluoroethylene and silicone rubber.

2. A biologically inert swab as defined in claim 1 wherein said swab element is provided with an internal bore which frictionally receives said one end of said elongated carrier member.

3. A biologically inert swab as defined in claim 1 wherein said elongated carrier member is constructed of thermoplastic material.

4. A biologically inert swab as defined in claim 3 wherein in said swab element is ultrasonically welded to said rod.

5. A biologically inert swab as defined in claim 1, wherein said elongated carrier and said swab element comprise a single, integrally molded unit.

6. A biologically inert swab as defined in claim 1, wherein said swab element is hydrophobic.

7. A biologically inert swab as defined in claim 1, wherein said swab element is hydrophylic.

8. Apparatus for collecting a biological specimen, said apparatus comprising:
    first and second coaxial members slidably movable with respect to each other through a predetermined distance in a first predetermined direction;
    first and second spaced apart flexible seal means being secured to said first coaxial member and slidably received within said second coaxial member to define a biological specimen collection zone therebetween;
    biological collection means secured to said first coaxial member between said first and second spaced apart flexible seals, said collection means comprising a porous molded plastic swab element formed with a pore size of about 10 to about 2,000 microns;
    third and fourth spaced apart seal means being secured to said second coaxial member and slidably receiving said first coaxial member therewithin to define two additional chambers within said coaxial members;
    said third and fourth seal means being spaced apart by a distance at least equal to said predetermined distance.

9. Apparatus as defined in claim 8 wherein one end of said first and second coaxial members includes connection means further comprising:
    first and second extension means respectively connectable to said connection means of the first and second coaxial members so as to extend the effective structural end thereof.

10. Apparatus as defined in claim 8 wherein said swab element has the density of about 35% to about 60% void volume.

11. Apparatus as defined in claim 8 wherein said swab element is constructed of plastic material selected from the group consisting essentially of high density polyethylene, ultra-high molecular weight polyethylene, polypropylene, polyvinyledene fluoride, ethylene-vinylacetate, styrene-acrylonitrile, polytetrafluoroethylene and silicone rubber.

12. Apparatus as defined in claim 8 wherein said swab element is friction fit to said first coaxial means.

13. Apparatus as defined in claim 8 wherein said first coaxial member is constructed of thermoplastic material.

14. Apparatus as defined in claim 3 wherein said swab element is ultrasonically welded to said first coaxial member.

15. A biologically inert swab as defined in claim 8, wherein said first coaxial member and said swab element comprise a single, integrally molded unit.

16. A biologically inert swab as defined in claim 8, wherein said swab element is hydrophobic.

17. A biologically inert swab as defined in claim 8, wherein said swab element is hydrophylic.

18. An instrument for obtaining a biological specimen, said instrument comprising:
   an outer hollow tube having first and second ends;
   an inner rod having first and second ends and disposed within said outer tube;
   a specimen capturing structure affixed to said inner rod, said specimen capturing structure including a porous, molded plastic swab element formed with a pore size of about 10 to about 2,000 microns;
   a rear seal affixed to the first end of said outer tube and in slidably sealed engagement with said inner rod;
   a front seal affixed to the second end of said inner rod and defining a sealed connection with the second end of said outer tube which may be controllably opened by sliding movement of said inner rod; and
   a middle seal affixed to the inner rod at a point between said rear seal and specimen capturing structures, said middle seal, defining a slidable sealed connection with the inside wall of said outer tube.

19. An instrument as defined in claim 18 wherein said swab element has the density of about 35% to about 60% void volume.

20. An instrument as defined in claim 18 wherein said swab element is constructed of plastic material selected from the group consisting essentially of high density polyethylene, ultra-high molecular weight polyethylene, polypropylene, polyninyledene fluoride, ethylene-vinylacetate, styrene-acrylonitrile, polytetrafluoroethylene and silicone rubber.

21. An instrument as defined in claim 18 wherein said swab element is friction fit to said inner rod.

22. An instrument as defined in claim 20 wherein said inner rod is formed of thermoplastic material.

23. An instrument as defined in claim 22 wherein said swab element is ultrasonically welded to said inner rod.

24. A biologically inert swab as defined in claim 20, wherein said inner rod and said swab element comprise a single, integrally molded unit.

25. A biologically inert swab as defined in claim 20, wherein said swab element is hydrophobic.

26. A biologically inert swab as defined in claim 20, wherein said swab element is hydrophylic.

* * * * *